United States Patent
Kawaura et al.

(10) Patent No.: US 10,258,374 B2
(45) Date of Patent: Apr. 16, 2019

(54) PUNCTURE APPARATUS

(71) Applicant: TERUMO KABUSHIKI KAISHA, Shibuya-ku (JP)

(72) Inventors: Masakatsu Kawaura, Sunnyvale, CA (US); Shigeki Ariura, Ebina (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 861 days.

(21) Appl. No.: 14/600,512

(22) Filed: Jan. 20, 2015

(65) Prior Publication Data
US 2015/0142040 A1    May 21, 2015

Related U.S. Application Data

(63) Continuation of application No. PCT/JP2012/068361, filed on Jul. 19, 2012.

(51) Int. Cl.
| | |
|---|---|
| *A61B 17/04* | (2006.01) |
| *A61B 17/34* | (2006.01) |
| *A61B 17/06* | (2006.01) |
| *A61B 17/062* | (2006.01) |

(Continued)

(52) U.S. Cl.
CPC .... *A61B 17/3468* (2013.01); *A61B 17/06109* (2013.01); *A61B 17/0482* (2013.01);
(Continued)

(58) Field of Classification Search
CPC ........ A61B 5/150503; A61B 5/150473; A61B 17/06; A61B 17/0469; A61B 17/3468;
(Continued)

(56) References Cited

U.S. PATENT DOCUMENTS

| | | | | |
|---|---|---|---|---|
| 4,799,495 A | * | 1/1989 | Hawkins | ............ A61B 17/3403 600/567 |
| 2003/0181924 A1 | * | 9/2003 | Yamamoto | ......... A61B 17/0467 606/144 |

(Continued)

FOREIGN PATENT DOCUMENTS

| | | |
|---|---|---|
| JP | 2003-225241 A | 8/2003 |
| JP | 2003-523786 A | 8/2003 |

(Continued)

OTHER PUBLICATIONS

International Search Report (PCT/ISA/210) dated Oct. 16, 2012, by the Japanese Patent Office as the International Searching Authority for International Application No. PCT/JP2012/068361.

*Primary Examiner* — Darwin P Erezo
*Assistant Examiner* — Erich Herbermann
(74) *Attorney, Agent, or Firm* — Buchanan Ingersoll & Rooney PC

(57) ABSTRACT

A puncture apparatus is disclosed, which can include a first puncture needle having a first needle tip and configured to puncture a living body tissue, a shaft interlocked to the first puncture needle, a second puncture needle having a second needle tip and configured to puncture a living body tissue, the second needle tip being oriented in a direction different from a direction in which the first needle tip is oriented, the second puncture needle being disposed so as to be movable relative to the first puncture needle in a proximal direction of the first puncture needle, and a moving section moving the second puncture needle relative to the first puncture needle in the proximal direction of the first puncture needle.

15 Claims, 9 Drawing Sheets

(51) Int. Cl.
   *A61B 17/42* (2006.01)
   *A61B 17/00* (2006.01)

(52) U.S. Cl.
   CPC ............ *A61B 17/062* (2013.01); *A61B 17/42* (2013.01); *A61B 2017/00805* (2013.01); *A61B 2017/06042* (2013.01); *A61B 2017/06057* (2013.01)

(58) Field of Classification Search
   CPC ............ A61B 17/06109; A61B 17/062; A61B 17/06066; A61B 2017/0472; A61B 2017/06057; A61B 17/32; A61B 17/3474; A61M 5/158; A61M 5/162; A61M 2005/1585
   USPC ........................................................ 606/222
   See application file for complete search history.

(56) References Cited

U.S. PATENT DOCUMENTS

| 2007/0213757 | A1* | 9/2007 | Boraiah ............ | A61B 17/0057 606/184 |
| 2008/0097190 | A1* | 4/2008 | Hornscheidt .... | A61B 17/06066 600/421 |

FOREIGN PATENT DOCUMENTS

| JP | 2005-518899 A | 6/2005 |
| JP | 2007-260385 A | 10/2007 |
| JP | 2010-099499 A | 5/2010 |
| WO | WO 2000/74594 A1 | 12/2000 |
| WO | WO 2003/075792 A1 | 9/2003 |

* cited by examiner

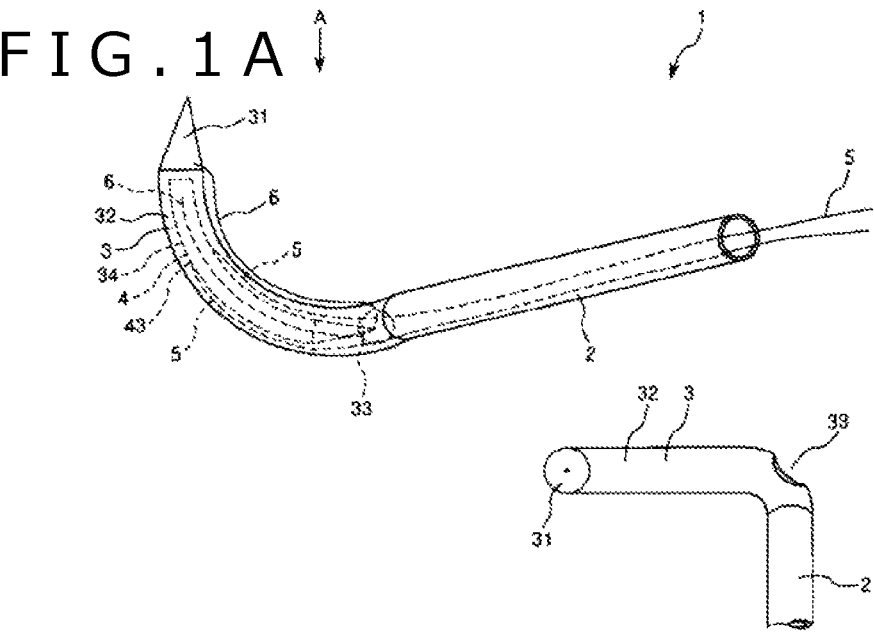
FIG. 1A
FIG. 1B
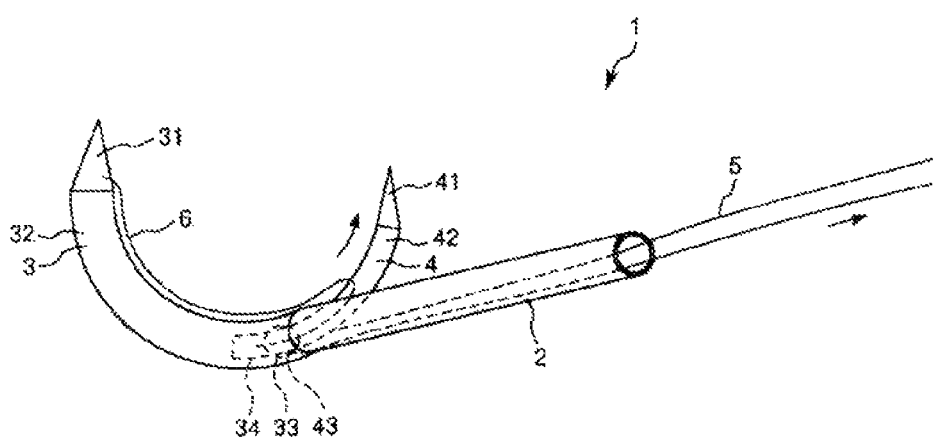
FIG. 2

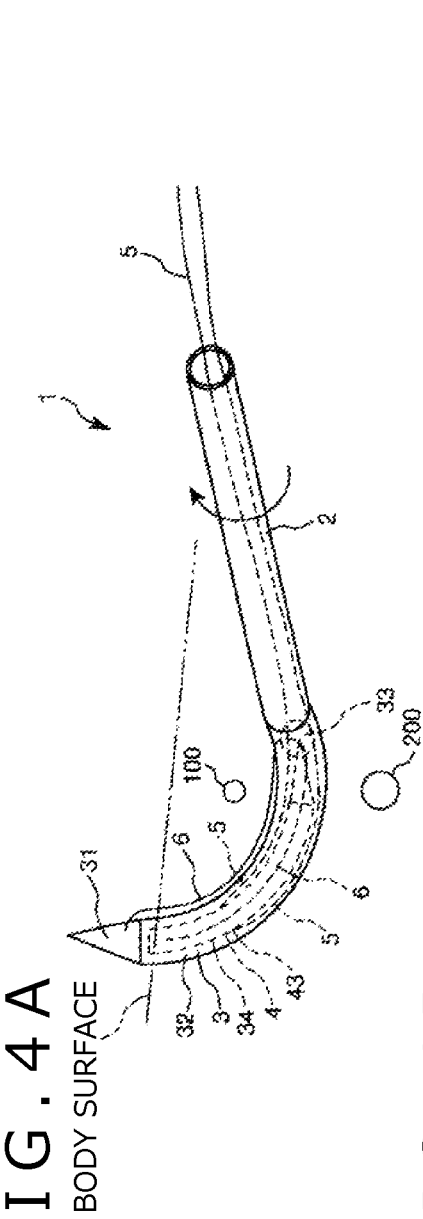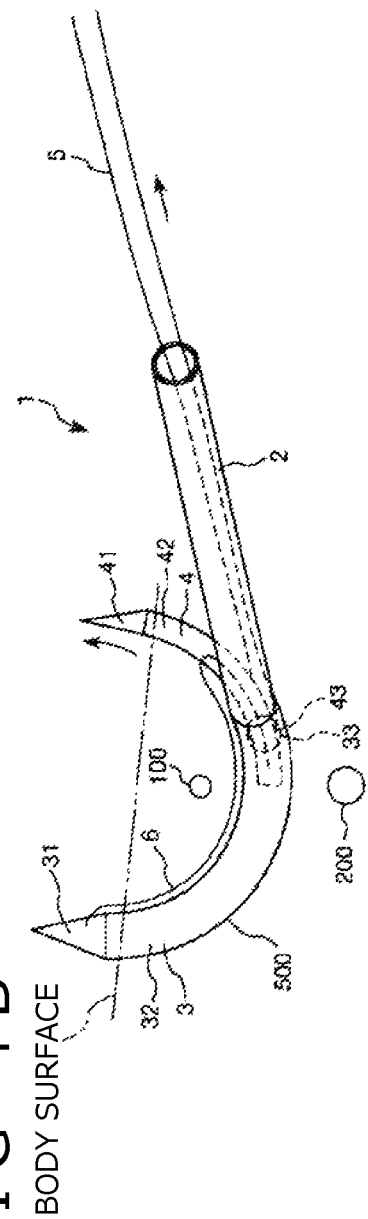

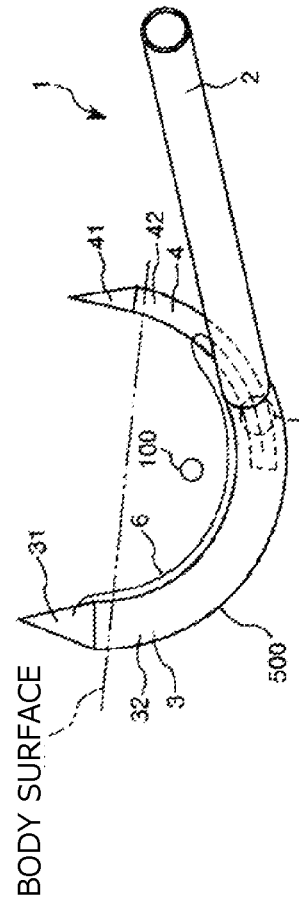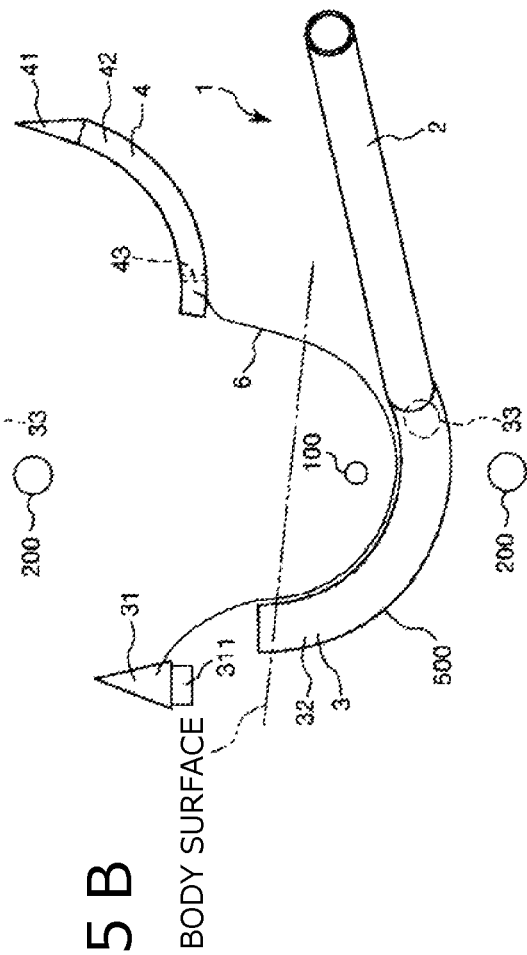
FIG. 5A
FIG. 5B

PUNCTURE APPARATUS

CROSS-REFERENCES TO RELATED APPLICATIONS

This application is a continuation of International Application No. PCT/JP2012/068361 filed on Jul. 19, 2012, the entire content of which is incorporated herein by reference.

TECHNICAL FIELD

The present disclosure generally relates to a puncture apparatus.

BACKGROUND

If a person suffers from a urinary incontinence, for example, if a person suffers from a stress urinary incontinence, then urine leakage can be caused by application of abdominal pressure during normal exercise or by laughing, coughing, sneezing, or the like. The cause of this may be, for example, that the pelvic floor muscle which is a muscle for supporting the urethra is loosened by birth.

For the treatment of urinary incontinence, a surgical treatment is effective, in which there is used, for example, a tape-shaped implant called a "sling." The sling is indwelled inside the body and the urethra is supported by the sling (see, for example, Japanese Patent Laid-Open No. 2010-99499). In order to indwell the sling inside the body, an operator would incise the vagina wall with a surgical knife, dissect a region between the urethra and the vagina, and make the dissected region and the outside communicate with each other through an obturator foramen of a pelvis by use of a puncture needle, forming a puncture hole. Then, by use of such a puncture hole, the sling is indwelled into the body.

If the vagina wall is once incised, however, there is a fear that there occurs a phenomenon in which the sling will be exposed to the inside of the vagina from a wound caused by the incision, and that complications can occur caused by an infection from the wound or the like. In addition, since the vagina wall is incised, the invasiveness of the procedure can be relatively great and burdensome on the patient. In addition, there is a risk that the urethra might be damaged in the course of the procedure by the operator and there is a risk that the operator might damage his/her fingertip with a surgical knife.

SUMMARY

In accordance with an exemplary embodiment, a puncture apparatus is disclosed that is able to reduce the relative burden on the patient with a relatively high degree of safety to both the patient and the operator.

In accordance with an exemplary embodiment, a puncture apparatus is disclosed, which can include a first puncture needle having a first needle tip and configured to puncture a living body tissue. The puncture apparatus can include a shaft interlocked to the first puncture needle. The puncture apparatus can include a second puncture needle having a second needle tip and configured to puncture a living body tissue. The second needle tip can be oriented in a direction different from a direction in which the first needle tip is oriented. The second puncture needle can be disposed to be movable relative to the first puncture needle in a proximal direction of the first puncture needle. The puncture apparatus further can include a moving section moving the second puncture needle relative to the first puncture needle in the proximal direction of the first puncture needle.

In accordance with an exemplary embodiment, the moving section has a traction wire for pulling the second puncture needle toward the second needle tip side.

In accordance with an exemplary embodiment, the moving section has a pushing member which has an elongated shape and is configured to push the second puncture needle toward the second needle tip side.

In accordance with an exemplary embodiment, the first puncture needle has a hollow portion. The second puncture needle is inserted in the hollow portion so that the second puncture needle is movable relative to the first puncture needle along a longitudinal direction of the first puncture needle.

In accordance with an exemplary embodiment, an opening communicating with the hollow portion of the first puncture needle is provided in a vicinity of an interlock portion between the first puncture needle and the shaft. The second puncture needle protrudes through the opening when the second puncture needle is moved relative to the first puncture needle in the proximal direction of the first puncture needle.

In accordance with an exemplary embodiment, the second puncture needle has a hollow portion into which the first puncture needle is inserted in a state where the first needle tip is protruding from the second puncture needle. The second puncture needle is disposed to be movable relative to the first puncture needle along a longitudinal direction of the first puncture needle.

In accordance with an exemplary embodiment, the second puncture needle has a slit formed along an axial direction of the second puncture needle, the slit being open to a proximal end of the second puncture needle.

In accordance with an exemplary embodiment, the puncture apparatus further includes a filamentous element which is connected to the first puncture needle on one end side of the filamentous element and is connected to the second puncture needle on other end side of the filamentous element.

In accordance with an exemplary embodiment, the first puncture needle includes a main body portion, and the first needle tip disposed at a distal portion of the main body portion in a separable manner. The filamentous element is connected to the first needle tip on the one end side of the first needle tip.

In accordance with an exemplary embodiment, the second puncture needle is separable from the first puncture needle.

In accordance with an exemplary embodiment, each of the first puncture needle and the second puncture needle has a region bent along a longitudinal direction of the first and second puncture needles.

In accordance with an exemplary embodiment, the first puncture needle is configured to puncture a living body tissue in a region between two living body lumens arranged side by side.

In accordance with an exemplary embodiment, the puncture apparatus further includes a restriction section restricting a puncturing direction of the first puncture needle.

In accordance with an exemplary embodiment, a method of forming a path in living body tissue is disclosed, the method comprising: puncturing a living body tissue with a first puncture needle having a first needle tip; and puncturing the living body tissue with a second puncture needle having a second needle tip, the second needle tip being oriented in a direction different from a direction in which the first needle tip is oriented, the second puncture needle being configured to be movable relative to the first puncture needle in a proximal direction of the first puncture needle.

BRIEF DESCRIPTION OF THE DRAWINGS

FIGS. 1A and 1B are views showing a first exemplary embodiment of the puncture apparatus according to the present disclosure;

FIG. 2 is a perspective view showing a state in which a rear puncture needle of the puncture apparatus shown in FIGS. 1A and 1B is protruded;

FIGS. 4A and 4B are views showing an operating procedure of the puncture apparatus shown in FIGS. 1A and 1B;

FIGS. 5A and 5B are views showing an operating procedure of the puncture apparatus shown in FIGS. 1A and 1B;

DETAILED DESCRIPTION

Now, the puncture apparatus according to the present disclosure will be described in detail below, referring to some exemplary embodiments of the disclosure shown in the accompanying drawings.

Figure 3:
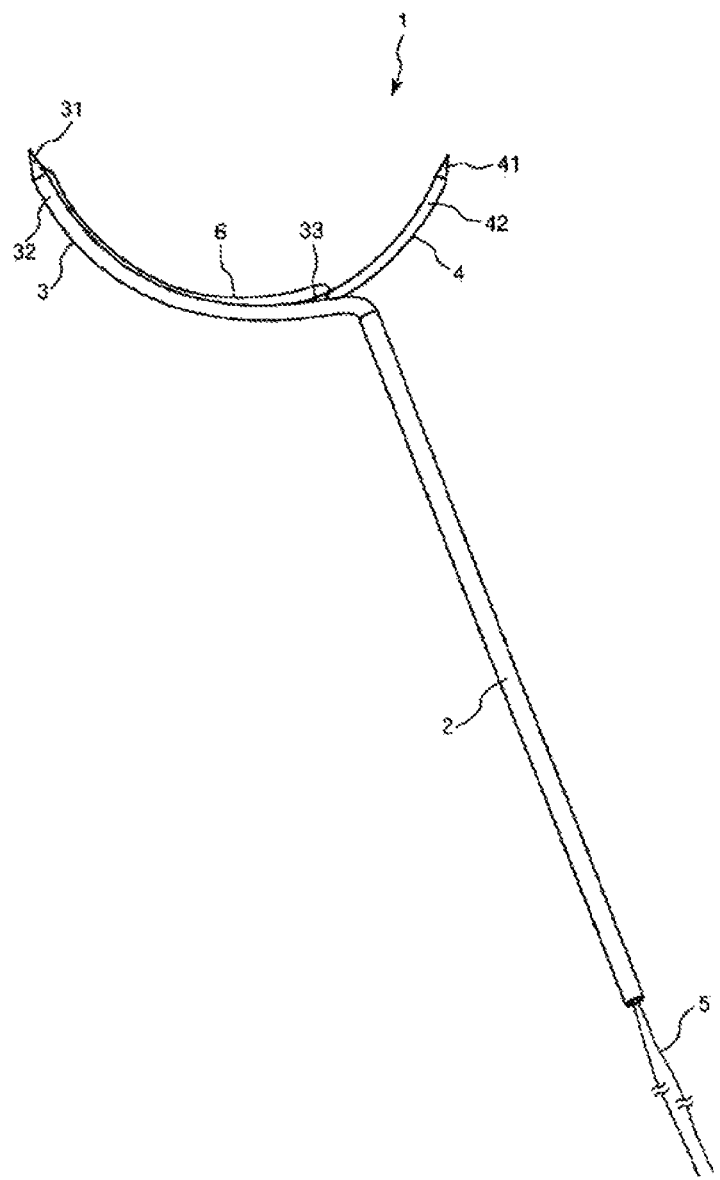
FIG. 3 is a perspective view of the puncture apparatus shown in FIG. 2.

FIGS. 1A and 1B are views showing a first embodiment of the puncture apparatus according to the present disclosure, wherein FIG. 1A is a perspective view and FIG. 1B is a view as viewed along arrow A in FIG. 1A. FIG. 2 is a perspective view showing a state in which a rear puncture needle of the puncture apparatus shown in FIGS. 1A and 1B is protruded. FIG. 3 is a perspective view showing the puncture apparatus shown in FIG. 2. FIGS. 4A to 6 are views for explaining an operating procedure of the puncture apparatus shown in FIGS. 1A and 1B.

In FIGS. 4A to 6, oblique lines (shading) indicative of living body tissue are omitted, for easier viewing. In addition, in FIGS. 4A to 5B, it is assumed that a string is inserted in an obturator foramen. FIGS. 1A, 1B, 2, and 4A to 6 are schematic views, in which the ratios of length to thickness (radial size) in regard of a front puncture needle, a rear puncture needle and a shaft are different from the actual ratios.

In the following description, with respect to the front puncture needle and along a longitudinal direction of the front puncture needle in FIGS. 1A to 5B, the side of a needle tip will be referred to as the "distal end" or the "front side," and the side opposite to the needle tip as the "proximal end" or the "rear end."

Regarding the front puncture needle and along a longitudinal direction of the front puncture needle in FIGS. 1A to 5B, the side of a needle tip will be referred to as the "distal end," and the side opposite to the tip needle as the "proximal end." Also, regarding the rear puncture needle and along a longitudinal direction of the rear puncture needle in FIGS. 1A to 5B, the side of a needle tip will be referred to as the "distal end," and the side opposite to the tip needle as the "proximal end." Concerning the shaft and along a longitudinal direction of the shaft in FIGS. 1A to 5B, the left side will be referred to as the "distal end," and the right side as the "proximal end."

In accordance with an exemplary embodiment, a puncture apparatus 1 shown in FIGS. 1-13 is an apparatus, which can be used in treatment of female urinary incontinence, for example, to be used at the time of implanting into a living body an implant (in-living-body indwelling instrument) for treatment of urinary incontinence.

The implant is an instrument, which is implantable for treatment of female urinary incontinence. In accordance with an exemplary embodiment, the implant is an instrument which can be implanted in a living body to support a urethra, for example, an instrument which supports the urethra in the manner of pulling the urethra in a direction for spacing away from a vaginal wall when the urethra would otherwise be going to move toward the vaginal wall. As the implant, there can be used, for example, a flexible elongated member.

Figure 6:
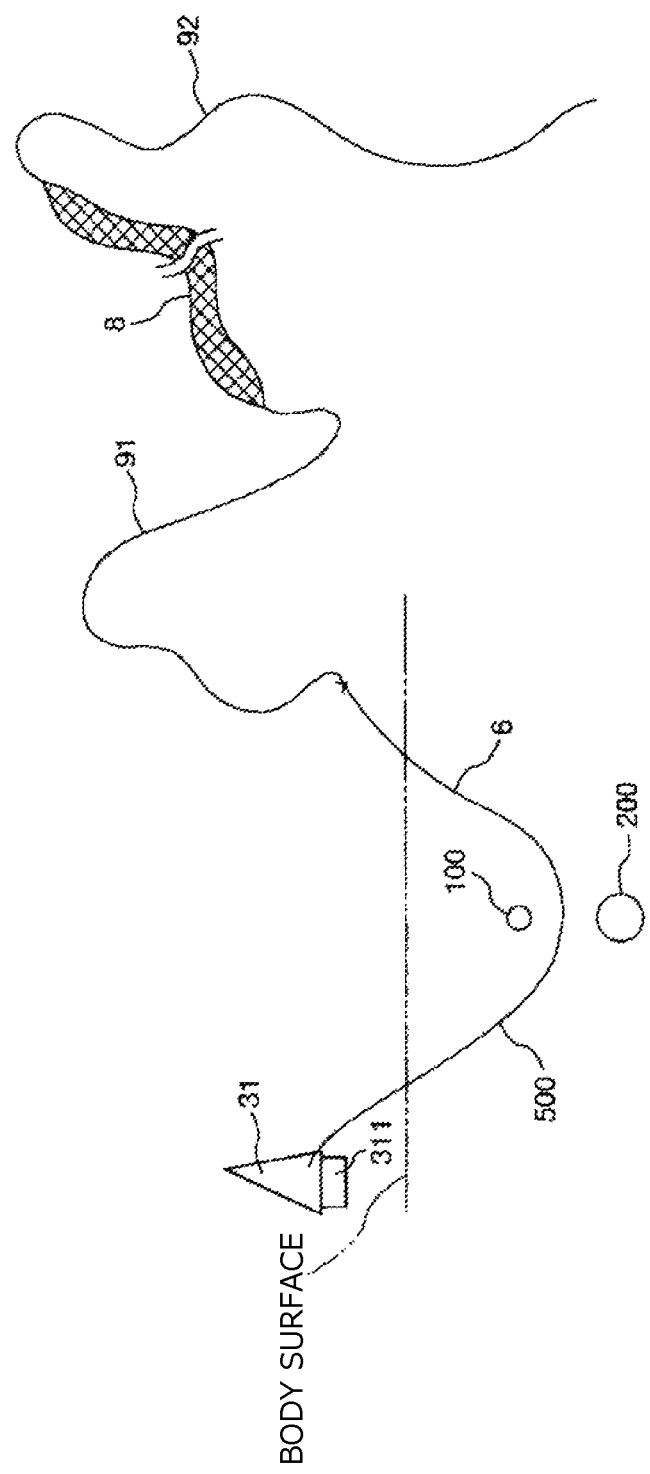
FIG. 6 is a view showing an operating procedure of the puncture apparatus shown in FIGS. 1A and 1B.

As shown in FIG. 6, an implant 8 in this exemplary embodiment is net-like in form and is band-like (ribbon-like) in overall shape. The implant 8 is called a "sling." The implant 8 may include a body knitted in a net form (lattice form) by intersection of filamentous elements, for example, including a net-like knitting. Examples of the filamentous elements include those, which are circular in cross-sectional shape, and those, which are flat in cross-sectional shape, for example, having a belt-like or ribbon-like shape. A one-side end of a string 91 can be fixed to one-side end of the implant 8, and a one-side end of a string 92 can be fixed to the other-side end of the implant 8.

The material constituting the implant 8 is not specifically restricted; examples of the material usable here include various biocompatible resin materials (for example, a polypropylene), their fibers and the like.

The material or materials constituting the strings 91 and 92 are not specifically restricted; examples of the material or materials applicable here include various biocompatible resin materials (for example, polypropylene), their fibers and the like.

In accordance with an exemplary embodiment, for example, the implant 8 is not restricted to the net-like ones.

As shown in FIGS. 1A to 3, the puncture apparatus 1 can include a front puncture needle (first puncture needle) 3 having a needle tip (first needle tip) 31 configured to puncture a living body tissue, a shaft 2 interlocked to the front puncture needle 3, a rear puncture needle (second puncture needle) 4 which is disposed so as to be movable relative to the front puncture needle 3 along a longitudinal direction of the front puncture needle 3 and which has a needle tip (second needle tip) 41 configured to puncture a living body tissue, a wire (traction wire) 5 as a moving section moving the rear puncture needle 4 relative to the front puncture needle 3 in a proximal direction of the front puncture needle 3, and a string (filamentous element) 6. A needle tip 41 of the rear puncture needle 4 can be oriented in a direction different from a direction in which the needle tip 31 of the front puncture needle 3 is oriented. The rear puncture needle 4 can be movable in the proximal direction of the front puncture needle 3, for example, toward the side opposite to the needle tip 31 of the front puncture needle 3.

In this exemplary embodiment, as will be described later, the front puncture needle 3 and the rear puncture needle 4 can be individually bent, and the rear puncture needle 4 can be moved in a proximal direction of the front puncture needle 3 along the bent axis of the front puncture needle 3. In accordance with an exemplary embodiment, the expression "the rear puncture needle 4 is moved in the proximal direction of the front puncture needle 3" can mean a concept that includes not only the case where the rear puncture needle 4 is moved on a straight line but also the case where the rear puncture needle 4 is moved on a curved line.

The front puncture needle 3 can include a main body portion 32, and the needle tip 31 disposed on a distal portion of the main body portion 32 in a freely detachable (separable) manner.

The main body portion 32 can be tubular in shape. In addition, the main body portion 32 can be bent in an arc shape along the longitudinal direction of the main body portion 32. Further, a proximal portion of the main body portion 32 can be bent in a direction different from the arc, as shown in FIGS. 1B and 3. In addition, an opening 33 communicating with a hollow portion 34 of the main body portion 32 can be formed in the vicinity of an interlock portion between the front puncture needle 3 and the shaft 2, in this embodiment at a wall portion of a proximal portion of the main body portion 32.

In addition, as shown in FIG. 5B, a reduced-diameter portion 311 that has an outside diameter slightly smaller than the inside diameter of the main body portion 32 can be formed at a proximal portion of the needle tip 31. In accordance with an exemplary embodiment, the reduced-diameter portion 311 can be fitted in a distal portion of the main body portion 32.

In accordance with an exemplary embodiment, the rear puncture needle 4 can include a main body portion 42, and the needle tip 41 fixed to a distal portion of the main body portion 42. The needle tip 41 and the main body portion 42 can be formed, for example, as one body (monolithically). In addition, the rear puncture needle 4 may be solid or may be hollow in a tubular shape.

In accordance with an exemplary embodiment, the main body portion 42 can be bent in an arc shape along the longitudinal direction of the main body portion 42. When a living body tissue is punctured by the front puncture needle 3 from a body surface in the vicinity of a region between a urethra and a vagina, therefore, the living body tissue between the urethra and the vagina can be punctured by the front puncture needle 3 relatively easily and reliably while avoiding a urethral wall and a vaginal wall. The radius of the arc of the main body portion 42 can be set approximately equal to the radius of the arc of the main body portion 32 of the front puncture needle 3.

In addition, the outside diameter of the main body portion 42 can be set smaller than the inside diameter of the main body portion 32 of the front puncture needle 3. In accordance with an exemplary embodiment, the rear puncture needle 4 is inserted in the hollow portion 34 of the front puncture needle 3 in such a manner that the rear puncture needle 4 can be movable relative to the front puncture needle 3 along the longitudinal direction of the front puncture needle 3 and is freely detachable in relation to the front puncture needle 3. When the rear puncture needle 4 is moved relative to the front puncture needle 3 in the proximal direction of the front puncture needle 3, the rear puncture needle 4 can protrude to the outside through the opening 33 of the front puncture needle 3.

In accordance with an exemplary embodiment, since the rear puncture needle 4 and the front puncture needle 3 are bent, the rear puncture needle 4 can be prevented from rotating relative to the front puncture needle 3 about an axis of the rear puncture needle 4.

The material or materials constituting the front puncture needle 3 and the rear puncture needle 4 are not specifically restricted, and examples of the material or materials usable here can include various metallic materials such as stainless steel, aluminum or aluminum alloys, titanium or titanium alloys, etc.

The string 6 is used in implanting the implant 8 into a living body, for example, in transporting the implant 8 into the living body. One-side end portion of the string 6 can be connected to the needle tip 31 of the front puncture needle 3, and the other-side end portion of the string 6 can be connected to a proximal portion of the rear puncture needle 4. In this exemplary embodiment, the string 6 can be disposed outside of the front puncture needle 3 and can be inserted into the hollow portion 34 through the opening 33.

The material constituting the string 6 is not particularly limited and examples of the material applicable here can include various resin materials, their fibers and the like.

In accordance with an exemplary embodiment, the shaft 2 can be tubular in shape, and a distal portion of shaft 2 can be bent. The distal end of the shaft 2 can be interlocked to the proximal end of the front puncture needle 3, and a lumen of the shaft 2 communicates with the hollow portion 34 of the front puncture needle 3.

The material constituting the shaft 2 is not specifically restricted, and examples of the material usable here can include various resin materials, various metallic materials and the like.

In accordance with an exemplary embodiment, the wire 5 can be for pulling and moving the rear puncture needle 4 toward the side of the needle tip 41 of the puncture needle 4 in relation to the front puncture needle 3, and can be connected to the rear puncture needle 4 in a freely detachable (separable) manner. For example, the rear puncture needle 4 can be formed with a through-hole 43 in a proximal portion of the puncture needle 4 (see FIG. 5B), and the wire 5 is inserted into and passed through the shaft 2 while being folded double in the state of being passed through the through-hole 43. In accordance with an exemplary embodiment, both end portions of the wire 5 can be protruding from the proximal end of the shaft 2 to the exterior. At the time of moving the rear puncture needle 4 toward its needle tip 41 side, both end portions of the wire 5 can be grasped and pulled in the proximal direction of the shaft 2.

The material constituting the wire 5 is not particularly limited, and examples of the material applicable here can include stainless steel, and superelastic alloys such as Ni—Ti alloys.

Now, an exemplary method of using the puncture apparatus 1 will be described below referring to FIGS. 4A to 6. Here, description will be made of a procedure taken until the implant 8 for treatment of female urinary incontinence is implanted into a living body by use of the puncture apparatus 1.

First, the shaft 2 of the puncture apparatus 1 is grasped, and the needle tip 31 of the front puncture needle 3 is made to puncture the living body from a body surface of a region in the vicinity of a base end of a patient's leg, for example, a region in the vicinity of a region between a labia majora and the leg base end (not shown) on the right side in FIG. 4A. Then, as shown in FIG. 4A, the shaft 2 is rotated clockwise in FIG. 4A. By this rotation of the shaft 2, the front puncture needle 3 is moved in the distal direction along the bent shape of the puncture needle 3, the needle tip 31 of the front puncture needle 3 is made to puncture a living body tissue between a urethra (living body lumen) 100 and a vagina (living body lumen) 200, for example, made to pass a region between the urethra 100 and the vagina 200, and further to pass an obturator foramen (not shown) on the left side in FIG. 4A of a pelvis, and is made to protrude from the body surface to the exterior of the body. In this embodiment, the opening 33 is located to the right side in FIG. 4A relative to the urethra 100 and the vagina 200 in a state in which the needle tip 31 of the front puncture needle 3 is protruding from the body surface to the exterior of the body.

Next, as shown in FIG. 4B, both end portions of the wire 5 are grasped and the wire 5 is pulled in the proximal direction of the shaft 2, without moving the front puncture needle 3. In accordance with an exemplary embodiment, it follows that the rear puncture needle 4 is moved along the longitudinal direction of the front puncture needle 3 in the distal direction of the rear puncture needle 4, for example, in the proximal direction of the front puncture needle 3, and the needle tip 41 of the rear puncture needle 4 passes an obturator foramen (not shown) on the right side in FIG. 4B of a pelvis to protrude from a body surface to the exterior of the body. In accordance with an exemplary embodiment, since the rear puncture needle 4 is located on the inner circumference side of the front puncture needle 3, the contact area between the rear puncture needle 4 and the living body tissue can be made comparatively small. Therefore, the rear puncture needle 4 can be moved easily and smoothly, and the burden on the patient can be lightened.

In this way, a puncture hole 500 for implanting the implant 8 in the living body is formed in the patient. This puncture hole 500 is a through-hole extending from a body surface of an inguinal region (not shown) on the left side in FIG. 4B or of a region in the vicinity of the inguinal region, passes the obturator foramen on the left side in the figure, passes between the urethra 100 and the vagina 200, and passes the obturator on the right side in the figure, to reach the body surface of the inguinal region (not shown) on the right side in FIG. 4B or of a region in the vicinity of the inguinal region.

While the opening 33 is located to the right side in FIG. 4A relative to the urethra 100 and the vagina 200 in the state where the needle tip 31 of the front puncture needle 3 is protruding from the body surface to the exterior of the body in this embodiment, this is not restrictive. The opening 33 may be located to the left side in FIG. 4A relative to the urethra 100 and the vagina 200, or may be located between the urethra 100 and the vagina 200. Where the opening 33 is located to the left side in FIG. 4A relative to the urethra 100 and the vagina 200, pulling the wire 5 in the proximal direction of the shaft 2 causes the needle tip 41 of the rear puncture needle 4 to puncture the living body tissue between the urethra 100 and the vagina 200. For example, the needle tip 41 passes between the urethra 100 and the vagina 200, and further passes the obturator foramen (not shown) on the right side in FIG. 4B of the pelvis, to protrude from the body surface to the exterior of the body.

Subsequently, as shown in FIG. 5A, with only one end portion of the wire 5 grasped, the wire 5 is pulled and drawn out in the proximal direction of the shaft 2.

Next, as shown in FIG. 5B, the needle tip 31 of the front puncture needle 3 is grasped, and is detached from the main body portion 32. In addition, the rear puncture needle 4 is grasped, and is moved in the proximal direction of the front puncture needle 3, thereby being separated from the front puncture needle 3 and drawn out of the patient.

Subsequently, the string 6 in the vicinity of either one of the needle tip 31 of the front puncture needle 3 and the rear puncture needle 4 is cut, and an end portion of either one of the string 91 and the string 92 on the implant 8 side is tied to an end portion of the string 6. In this exemplary embodiment, as an example, as shown in FIG. 6, the string 6 in the vicinity of the rear puncture needle 4 is cut, and an end portion of the string 91 is tied to an end portion of the string 6.

For example as shown in FIG. 4A, a procedure may be taken in which after the protrusion of the needle tip 31 of the front puncture needle 3 from the body surface to the exterior of the body, the needle tip 31 is detached from the main body portion 32, the string 6 in the vicinity of the needle tip 31 is cut, and an end portion of the string 91 or the string 92 on the implant 8 side is tied to an end portion of the string 6.

Next, the needle tip 31 of the front puncture needle 3 is grasped and pulled, to insert the implant 8 into the puncture hole 500 formed in the patient, and an end portion on the left side in FIG. 6 of the implant 8 is drawn out through the puncture hole 500 to the exterior of the body, in a state in which an end portion on the right side in FIG. 6 of the implant 8 is left in the exterior of the body.

Subsequently, each of the strings 91 and 92 is pulled with the predetermined force, to adjust the position of the implant 8 relative to the urethra 100, then unnecessary portions of the implant 8 are cut away, and a predetermined treatment is carried out, to finish the procedure.

As has been described above, according to the puncture apparatus 1, implanting of the implant 8 into a living body can be dealt with by only a low invasive procedure such as puncturing with the front puncture needle 3 and the rear puncture needle 4, without need for considerably invasive incision or the like. Consequently, the burden on the patient is relatively light, and the safety of the patient is relatively high.

For example, since the puncture apparatus 1 has the front puncture needle 3 and the rear puncture needle 4, the puncture hole 500 can be formed by puncturing the living body tissue from the body surface in the vicinity of a region between the urethra and the vagina by the front puncture needle 3 and further using the rear puncture needle 4. In accordance with an exemplary embodiment, since the living body tissue can be punctured from the body surface in the vicinity of the region between the urethra and the vagina by the front puncture needle 3, the living body tissue between the urethra and the vagina can be punctured by the front puncture needle 3 relatively easily and assuredly, while avoiding the urethral wall and the vaginal wall. Thus, according to the puncture apparatus 1, puncturing of the urethral wall and puncturing of the vaginal wall can both be prevented from occurring, which can provide relative safety and relatively easy and reliable formation of the puncture hole 500.

In addition, since the operator need not perform incision or the like, damaging of the operator's fingertip with a surgical knife or the like can be prevented, and safety can be relatively secured.

While the puncture hole formed in the patient by the puncture needle is a through-hole in this embodiment, this is not restrictive. The puncture hole may not be of the penetrating (passing-through) type.

While the shaft 2 has its distal portion in a bent form in this embodiment, this configuration is not restrictive; for example, the shaft 2 may be straight line-like in overall shape.

In addition, each of the front puncture needle 3 and the rear puncture needle 4 may have, for example, a structure in which only part of the structure is bent in an arc shape or a structure in which the whole part of the structure is bent in an arc shape. For example, each of the front puncture needle 3 and the rear puncture needle 4 can have an arc-shaped bent region at least at part of the front puncture needle 3 and the rear puncture needle 4. In addition, the shape of the bent region of each of the front puncture needle 3 and the rear puncture needle 4 is not restricted to an arc shape.

Figure 7A:
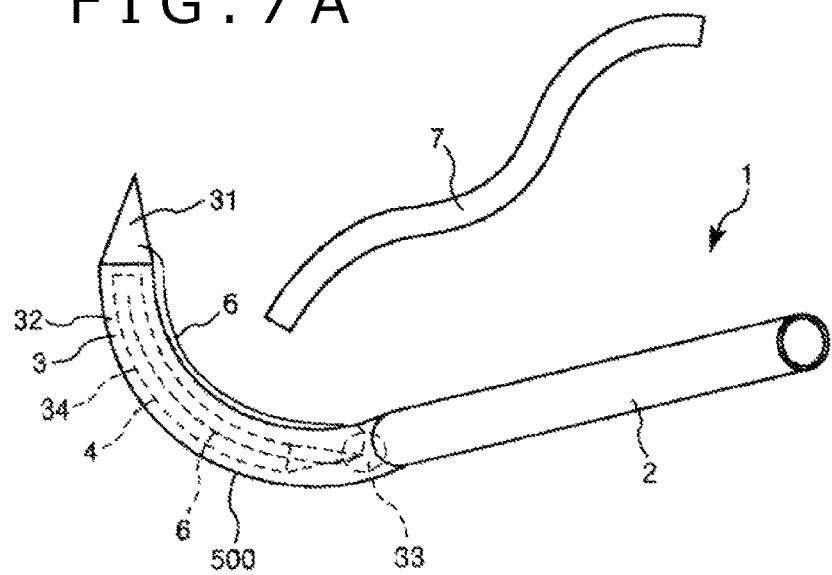
FIGS. 7A and 7B are perspective views showing a second exemplary embodiment of the puncture apparatus according to the present disclosure.
Figure 7B:
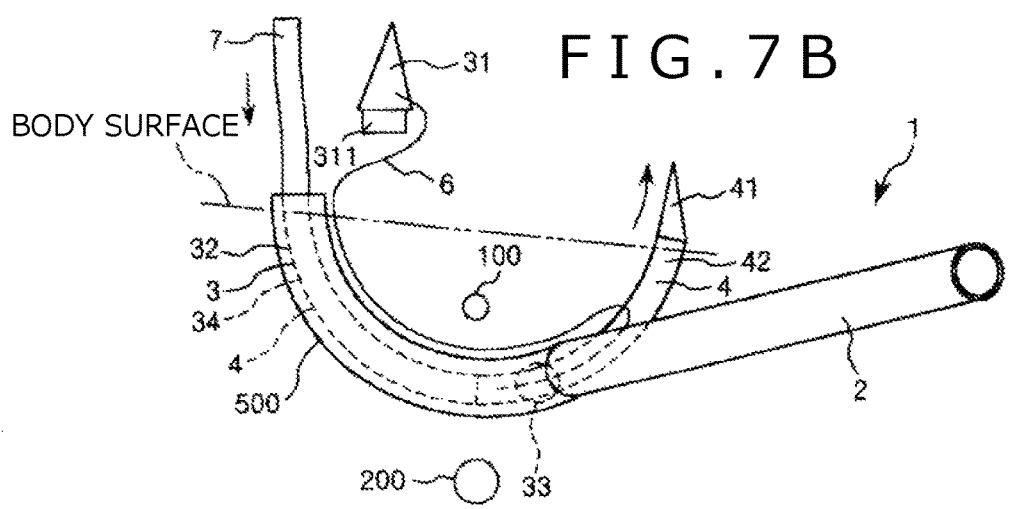

FIGS. 7A and 7B are perspective views showing a second exemplary embodiment of the puncture apparatus according to the present disclosure. In FIG. 7B, oblique lines (shading) indicative of living body tissue are omitted for relatively easier viewing and a string can be inserted in an obturator foramen. In addition, FIGS. 7A and 7B are schematic views, in which the ratios of length to thickness (radial size) with respect to a front puncture needle, a rear puncture needle and a shaft are different from the actual ratios.

In the following description, along a longitudinal direction of the front puncture needle in FIGS. 7A and 7B, the side of a needle tip of the front puncture needle will be referred to as the "distal end" or the "front side," and the side opposite to the needle tip as the "proximal end" or the "rear side." In addition, with respect to the front puncture needle and along the longitudinal direction of the front puncture needle in FIGS. 7A and 7B, the side of the needle tip will be referred to as the "distal end," and the side opposite to the needle tip as the "proximal end." Concerning the rear puncture needle and along the longitudinal direction of the rear puncture needle in FIGS. 7A and 7B, the side of the needle tip will be referred to as the "distal end," and the side opposite to the needle tip as the "proximal end." In regard of the shaft and along the longitudinal direction of the shaft in FIGS. 7A and 7B, the left side will be referred to as the "distal end," and the right side as the "proximal end."

Now, the second exemplary embodiment will be described below, mainly regarding its differences from the aforementioned first embodiment, while descriptions of the same or equivalent items to those described above will be omitted.

As shown in FIG. 7A, a puncture apparatus 1 according to the second exemplary embodiment can have, in place of the aforementioned wire 5 as the moving section, a pusher (pushing member) 7 which can be elongated in shape and can be configured to push and move a rear puncture needle 4 in a direction toward a needle tip 41 of the rear puncture needle 4. In accordance with exemplary embodiment, the pusher 7 can have both such a degree of flexibility as to be elastically deformable in conformity with the shape of a front puncture needle 3 and such a degree of rigidity as to be able to push and move the rear puncture needle 4.

When moving the rear puncture needle 4 by use of the pusher 7, as shown in FIG. 7B, the pusher 7 is inserted into a hollow portion 34 of the front puncture needle 3 through an opening at the distal end of a main body portion 32 of the front puncture needle 3, and is advanced. As a result, the rear puncture needle 4 is pushed by the pusher 7 to move along the longitudinal direction of the front puncture needle 3 in the distal direction of the rear puncture needle 4, for example, in the proximal direction of the front puncture needle 3. In this case, the needle tip 41 of the rear puncture needle 4 passes an obturator foramen (not shown) on the right side in FIG. 7B of a pelvis, to protrude from a body surface to the exterior of the body.

The material constituting the pusher 7 is not specifically restricted; for example, various resin materials and various metallic materials and the like can be used.

According to this puncture apparatus 1, the same or similar effects to those obtained in the aforementioned first embodiment can be obtained.

The second exemplary embodiment is also applicable to third to fifth exemplary embodiments, which will be described later.

Figure 8:
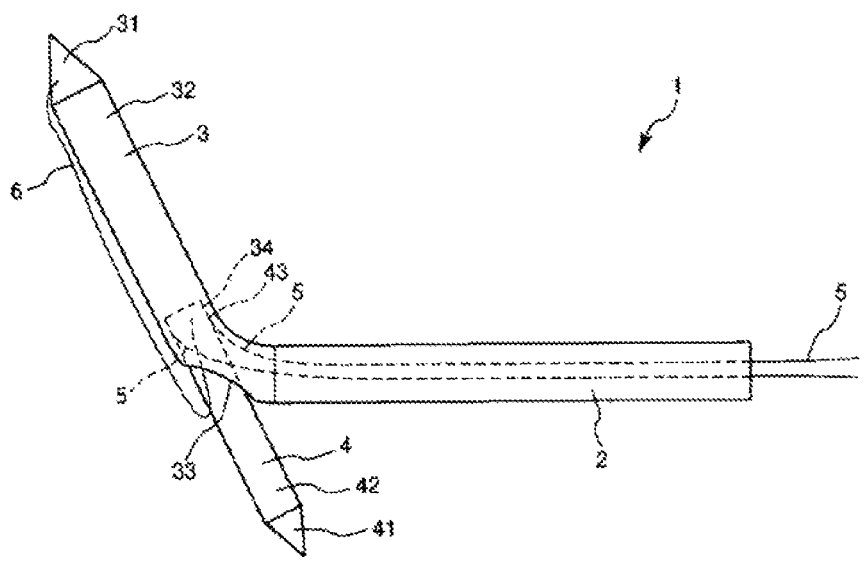
FIG. 8 is a side view showing a third exemplary embodiment of the puncture apparatus according to the present disclosure.

FIG. 8 is a side view showing a third exemplary embodiment of the puncture apparatus according to the present disclosure. FIG. 8 is a schematic view, in which the ratios of length to thickness (radial size) with respect to a front puncture needle, a rear puncture needle and a shaft are different from the actual ratios.

The third exemplary embodiment will now be described below, mainly regarding its differences from the aforementioned first embodiment, while descriptions of the same or equivalent items to those described above will be omitted.

As shown in FIG. 8, in a puncture apparatus 1 in the third exemplary embodiment, a front puncture needle 3 is not bent but is straight line-like in shape, except for its proximal portion. In addition, a rear puncture needle 4 is not bent but is straight line-like in shape.

According to this puncture apparatus 1, the same or similar effects to those obtained in the aforementioned first exemplary embodiment can be obtained.

The third exemplary embodiment is also applicable to the aforementioned second exemplary embodiment and a fifth exemplary embodiment, which will be described later.

Figure 9:
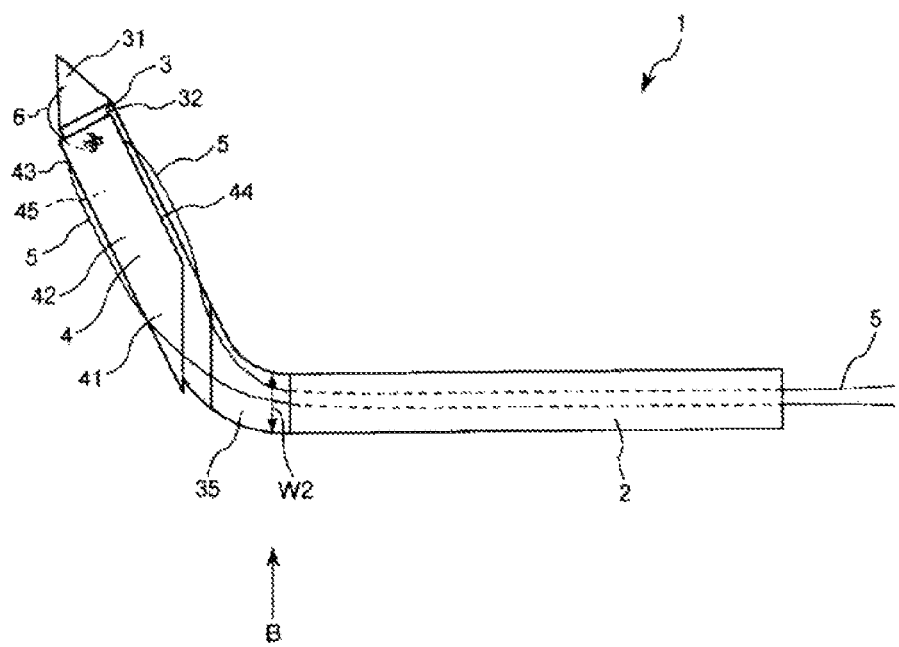
FIG. 9 is a side view showing a fourth exemplary embodiment of the puncture apparatus according to the present disclosure.
Figure 10:
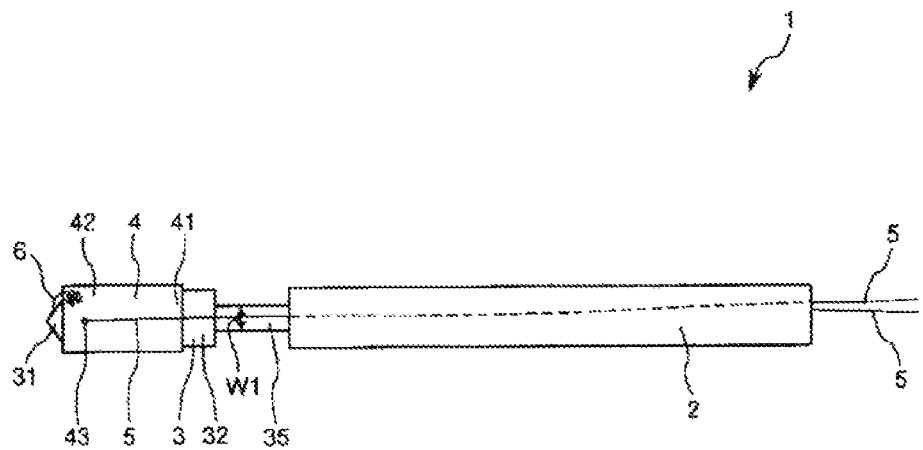
FIG. 10 is a view, as viewed along arrow B in FIG. 9, of the puncture apparatus shown in FIG. 9.
Figure 11:
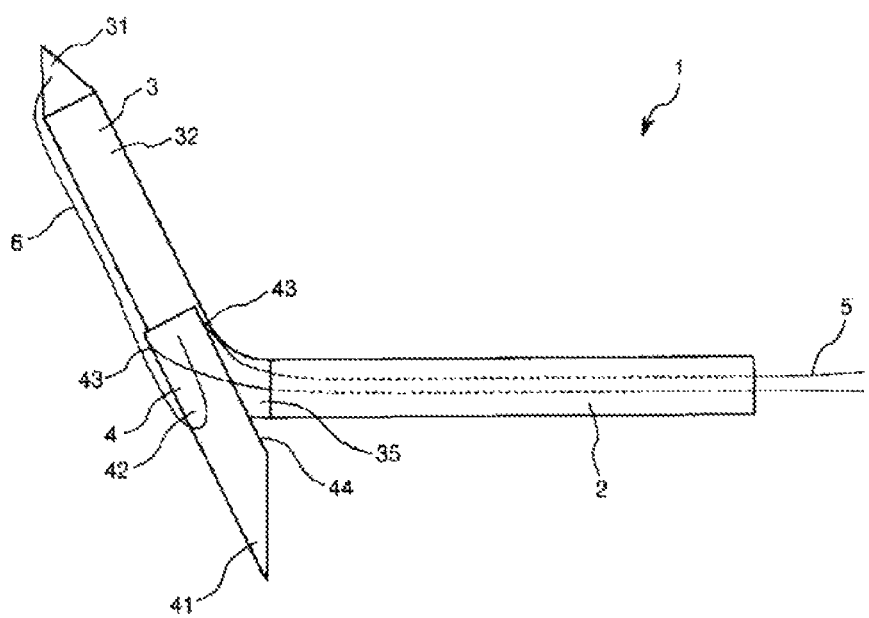
FIG. 11 is a side view showing a state in which a rear puncture needle of the puncture apparatus shown in FIG. 9 is protruded.

FIG. 9 is a side view showing a fourth exemplary embodiment of the puncture apparatus according to the present disclosure. FIG. 10 is a view, as viewed along arrow B in FIG. 9, of the puncture apparatus shown in FIG. 9. FIG. 11 is a side view showing a state in which a rear puncture needle of the puncture apparatus shown in FIG. 9 is protruded. FIGS. 9 to 11 are schematic views, in which the ratios of length to thickness (radial size) with respect to a front puncture needle, a rear puncture needle and a shaft are different from the actual ratios.

In the following description, along a longitudinal direction of the front puncture needle in FIGS. 9 to 11, the side of a needle tip of the front puncture needle will be referred to as the "distal end" or the "front side," and the side opposite to the needle tip as the "proximal end" or the "rear side." In addition, with respect to the front puncture needle and along the longitudinal direction of the front puncture needle in FIGS. 9 to 11, the side of the needle tip will be referred to as the "distal end," and the side opposite to the needle tip as the "proximal end." Concerning the rear puncture needle and along the longitudinal direction of the rear puncture needle in FIGS. 9 to 11, the side of the needle tip will be referred to as the "distal end," and the side opposite to the needle tip as the "proximal end." In regard of the shaft and along the longitudinal direction of the shaft in FIGS. 9 to 11, the left side will be referred to as the "distal end," and the right side as the "proximal end."

Now, the fourth exemplary embodiment will be described below, mainly regarding its differences from the aforementioned third embodiment, while descriptions of the same or equivalent items to those described above will be omitted.

As shown in FIGS. 9 to 11, in a puncture apparatus 1 according to the fourth exemplary embodiment, a rear puncture needle 4 is tubular in shape. A front puncture needle 3 is inserted in a hollow portion 45 of the rear puncture needle 4 in a state in which a needle tip 31 of the front puncture needle 3 is protruding from the proximal end of the rear puncture needle 4 to the outside.

In accordance with an exemplary embodiment, the front puncture needle 3 can be inserted in the hollow portion 45 of the rear puncture needle 4 so that the front puncture needle 3 can be moved relative to the rear puncture needle 4 along the longitudinal direction of the rear puncture needle 4. For example, the rear puncture needle 4 can be disposed on an outer circumferential surface of the front puncture needle 3 in such a manner that the rear puncture needle 4 is movable along the longitudinal direction of the front puncture needle 3 and is freely detachable.

In addition, a main body portion 32 of the front puncture needle 3 can have a plate-shaped bent region 35 at a proximal portion of the main body portion 32, and a proximal end of the bent region 35 and a distal end of a shaft 2 are interlocked to each other. In accordance with an exemplary embodiment, the bent region 35 can be so formed that a width of the bent region 35 in a direction perpendicular to the sheet plane of FIG. 9, namely, its width W1 in FIG. 10, is smaller than its width W2 in the vertical direction in FIG. 9. In addition, the width W1 of the bent region 35 can be smaller than the diameter of the main body portion 32 on the more distal side than the bent region 35, and the width W2 of the bent region 35 can be equal to the diameter of the main body portion 32 on the more distal side than the bent region 35.

In accordance with an exemplary embodiment, the rear puncture needle 4 has a slit 44 formed along an axial direction of the rear puncture needle 4, on the right upper side in FIG. 9. The slit 44 is formed to extend from the distal end to the proximal end of the rear puncture needle 4. For example, the slit 44 can be open to the proximal end and the distal end of the rear puncture needle 4. In addition, the width of the slit 44 in a direction perpendicular to the sheet plane of FIG. 9 is set greater than the width W1 of the bent region 35, which helps ensure that by moving the rear puncture needle 4 in the proximal direction of the front puncture needle 3, the rear puncture needle 4 can be separated from the front puncture needle 3.

According to this puncture apparatus 1, the same or similar effects to those obtained in the aforementioned third exemplary embodiment can be obtained.

The fourth exemplary embodiment is also applicable to the aforementioned first and second exemplary embodiments and a fifth exemplary embodiment, which will be described later.

Figure 12:
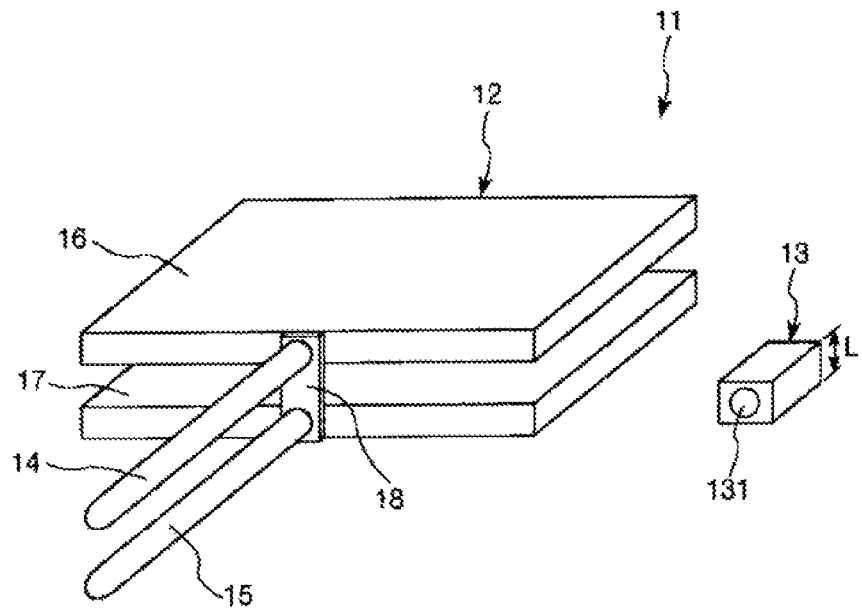
FIG. 12 is a perspective view of a guiding device in a fifth exemplary embodiment of the puncture apparatus according to the present disclosure.
Figure 13:
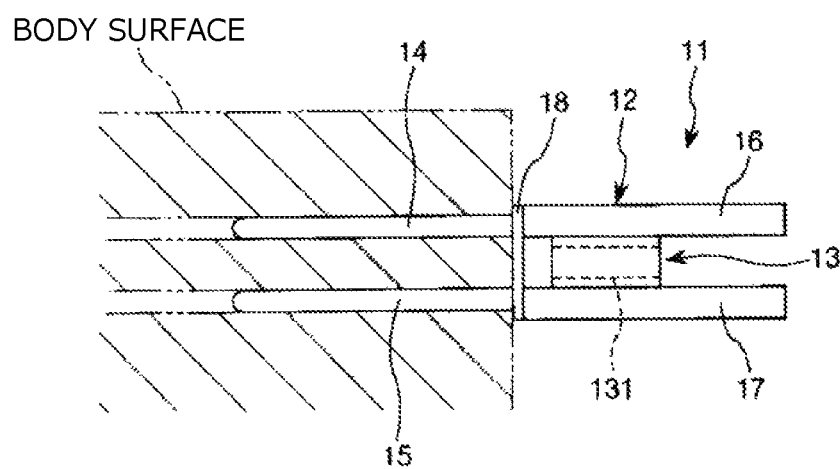
FIG. 13 is a view showing an exemplary use of the guiding device shown in FIG. 12.

FIG. 12 is a perspective view showing a guiding device in a fifth exemplary embodiment of the puncture apparatus according to the present disclosure. FIG. 13 is a view showing an exemplary use of the guiding device shown in FIG. 12. FIGS. 12 and 13 are schematic views, in which the ratios of length to thickness (radial size) with respect to a urethral-insertion portion and a vaginal-insertion portion are different from the actual ratios. In the following description, the left side in FIGS. 12 and 13 will be referred to as the "distal end," and the right side in the figures as the "proximal end."

Now, the fifth exemplary embodiment will be described below, mainly regarding its differences from the aforementioned first embodiment, and descriptions of the same or equivalent items to those described above will be omitted.

As shown in FIGS. 12 and 13, a puncture apparatus 1 in the fifth embodiment can include a guiding device 11 as a restriction section restricting puncturing directions of a front puncture needle 3 and a rear puncture needle 4. In addition, the guiding device 11 can include a guiding device main body 12 and a guide member 13.

The guiding device main body 12 can include an elongated urethral-insertion portion 14 to be inserted into a urethra, an elongated vaginal-insertion portion 15 to be inserted into a vagina, a pair of guide plates 16 and 17, and a supporting portion 18 for supporting the urethral-insertion portion 14 and the vaginal-insertion portion 15.

The guide plates 16 and 17 can be flat plates, which are so arranged that they are spaced from each other by a predetermined distance and are parallel to each other. The guide plate 16 is located on the upper side, in FIG. 12, of the guide plate 17. The respective shapes of the guide plates 16 and 17 are not specifically restricted in this exemplary embodiment, for example, the guide plates 16, 17 can be rectangular.

The supporting portion 18 is fixed to predetermined end faces of the guide plates 16 and 17, whereby the state in which the guide plates 16 and 17 are spaced by the predetermined distance from each other is maintained.

The urethral-insertion portion 14, in this exemplary embodiment, is firmly attached to the supporting portion 18 at a position corresponding to the guide plate 16. The urethral-insertion portion 14 can be formed in a straight bar-like shape from a non-flexible rigid material, and is so arranged that its axis is parallel to the guide plate 16. In accordance with an exemplary embodiment, a distal end portion of the urethral-insertion portion 14 can be rounded, which helps enable smooth insertion of the urethral-insertion portion 14 into a urethra.

The vaginal-insertion portion 15, in this exemplary embodiment, is firmly attached to the supporting portion 18 at a position corresponding to the guide plate 17. The vaginal-insertion portion 15 can be straight bar-like in shape, and can be so arranged that an axis of the vaginal-insertion portion 15 is parallel to the guide plate 17. In accordance with an exemplary embodiment, the axis of the vaginal-insertion portion 15 and the axis of the urethral-insertion portion 14 are parallel to each other. In addition, a distal end portion of the vaginal-insertion portion 15 can be rounded, which helps enable smooth insertion of the vaginal-insertion portion 15 into a vagina.

In accordance with an exemplary embodiment, the separated distance between the guide plate 16 and the guide plate 17 of the guiding device main body 12 and the separated distance between the urethral-insertion portion 14 and the vaginal-insertion portion 15 can be equal. Therefore, when the urethral-insertion portion 14 is inserted in the urethra and the vaginal-insertion portion 15 is inserted in the vagina, the region between the guide plate 16 and the guide plate 17 corresponds to the region between the urethra and the vagina.

The guide member 13, in this exemplary embodiment, can be rectangular parallelepiped in shape, and can include a through-hole 131. The guide member 13 can be used with the shaft 2 inserted in the through-hole 131.

In addition, the height L of the guide member 13 can be set to be substantially equal to or slightly smaller than the separated distance between the guide plate 16 and the guide plate 17.

The guide member 13 is used in the state of being inserted between the guide plate 16 and the guide plate 17, as shown in FIG. 13.

The respective materials constituting the urethral-insertion portion 14, the vaginal-insertion portion 15, the guide plates 16 and 17, the supporting portion 18, and the guide member 13 are not specifically restricted; for example, various resin materials and the like can be used.

When using the guiding device 11, the shaft 2 is inserted into the through-hole 131 of the guide member 13, and the guide member 13 is inserted between the guide plate 16 and the guide plate 17. Then, the shaft 2 is moved together with the guide member 13, or the shaft 2 is moved with the through-hole 131 as a guide while keeping the guide member 13 fixed in relation to the guide plates 16 and 17, or both of these operations are jointly conducted. As a result, the front puncture needle 3 and the rear puncture needle 4 are moved in a range corresponding to the region between the guide plate 16 and the guide plate 17. Thus, the front puncture needle 3 and the rear puncture needle 4 can be prevented from puncturing a urethral wall or a vaginal wall.

According to this puncture apparatus 1, the same or similar effects to those described in the aforementioned first embodiment can be obtained.

The fifth exemplary embodiment is also applicable to the aforementioned second to fourth exemplary embodiments.

While the puncture apparatus according to the present disclosure has been described above referring to some embodiments thereof illustrated in the drawings, the disclosure is not limited to the embodiments. Each of the components of the puncture apparatus may be replaced with one having an arbitrary configuration that has the same or equivalent function. For example, In accordance with an exemplary embodiments, other arbitrary configurations may be added to the configurations of the present disclosure.

In addition, the present disclosure may be a combination of arbitrary two or more configurations of the exemplary embodiments described above.

The cross-sectional shape of an inner circumferential surface of the front puncture needle and the cross-sectional shape of an outer circumferential surface of the rear puncture needle may each be non-circular, for example. In accordance with an exemplary embodiment, this configuration can help prevent the rear puncture needle from rotating relative to the front puncture needle about an axis of the rear puncture needle.

While the case where the puncture apparatus according to the present disclosure is applied to an apparatus used when implanting in a living body an implant for treatment of female urinary incontinence has been described in the above embodiments, this is not limitative of the use of the puncture apparatus of the disclosure.

According to the present disclosure, it can be relatively ensured, for example, that an implant can be implanted into a living body with relatively little burden on the patient, relatively high safety of the patient and the operator.

For instance, the use of the puncture apparatus of the present disclosure for treatment of female urinary incontinence help ensure that when implanting an implant for treatment of the urinary incontinence, the implanting operation can be carried out with a low invasive procedure, without needing incision of a vaginal wall. In addition, a phenomenon in which, like in the case of incision of a vagina wall, the implant would be exposed to the inside of the vagina from a wound caused by the incision and in which there would occur complications which are to be caused by an infection from the wound or the like can be prevented. Thus, very high safety can be secured and the implant can be reliably implanted.

In addition, since the puncture apparatus according to the present disclosure has the front puncture needle and the rear puncture needle, a puncture hole for implanting an implant can be formed by puncturing a living body tissue from a body surface in the vicinity of a region between the urethra and the vagina by the front puncture needle and further using the rear puncture needle. In accordance with an exemplary embodiment, by puncturing the living body tissue from the body surface in the vicinity of the region between the urethra and the vagina by the front puncture needle, the living body tissue between the urethra and the vagina can be punctured by the front puncture needle relatively easily and reliably, while avoiding the urethral wall and the vaginal wall.

In addition, since the operator need not perform incision or the like, damaging of the operator's fingertip with a surgical knife or the like can be prevented, and safety is secured. Accordingly, the puncture apparatus of the present disclosure has industrial applicability.

It should be understood by those skilled in the art that various modifications, combinations, sub-combinations and alterations may occur depending on design requirements and other factors insofar as they are within the scope of the appended claims or the equivalents thereof.

The detailed description above describes a puncture apparatus. The disclosure is not limited, however, to the precise embodiments and variations described. Various changes, modifications, and equivalents can effected by one skilled in the art without departing from the spirit and scope of the disclosure as defined in the accompanying claims. It is expressly intended that all such changes, modifications, and equivalents which fall within the scope of the claims are embraced by the claims.

What is claimed is:

1. A puncture apparatus comprising:
   a first puncture needle having a first needle tip and configured to puncture a living body tissue, the first puncture needle having a distal end and a proximal end, the first needle tip being on the distal end of the first puncture needle and being detachable from the first puncture needle;
   a shaft interlocked to the first puncture needle;
   a second puncture needle having a second needle tip and configured to puncture the living body tissue, the second needle tip being oriented in a direction different from a direction in which the first needle tip is oriented, the second puncture needle being configured to be detachable in relation to the first puncture needle and movable relative to the first puncture needle in a proximal direction of the first puncture needle when the second needle tip punctures the living body tissue, wherein the first puncture needle has a hollow portion, the second puncture needle is inserted in the hollow portion so that the second puncture needle is movable relative to the first puncture needle along a longitudinal direction of the first puncture needle, and the first puncture needle having a region bent along the longitudinal direction of the first puncture needle and the second puncture needle having a region bent along a longitudinal direction of the second puncture needle; and
   a moving section moving the second puncture needle relative to the first puncture needle in the proximal direction of the first puncture needle.

2. The puncture apparatus according to claim 1, wherein the moving section has a traction wire for pulling the second puncture needle toward the second needle tip.

3. The puncture apparatus according to claim 1, wherein the moving section has a pushing member which has an elongated shape and is configured to push the second puncture needle toward the second needle tip.

4. The puncture apparatus according to claim 1, comprising:
   an opening communicating with the hollow portion of the first puncture needle in a vicinity of an interlock portion between the first puncture needle and the shaft; and
   the second puncture needle being configured to protrude through the opening when the second puncture needle is moved relative to the first puncture needle in the proximal direction of the first puncture needle.

5. The puncture apparatus according to claim 1, comprising:
   a filamentous element which is connected to the first puncture needle on one end side of the first puncture needle and is connected to the second puncture needle on other end side of the first puncture needle.

6. The puncture apparatus according to claim 5, wherein the first puncture needle includes a main body portion;
   the first needle tip is disposed at a distal portion of the main body portion in a separable manner; and
   the filamentous element is connected to the first needle tip on the one end side of the first puncture needle.

7. The puncture apparatus according to claim 1, wherein the first puncture needle is configured to puncture the living body tissue in a region between two living body lumens arranged side by side.

8. The puncture apparatus according to claim 1, comprising:
   a restriction section restricting a puncturing direction of the first puncture needle.

9. A puncture apparatus comprising:
   a first puncture needle having a first needle tip and configured to puncture a living body tissue, the first puncture needle having a hollow portion, the first puncture needle having a distal end and a proximal end, the first needle tip being on the distal end of the first puncture needle and being detachable from the first puncture needle;
   a second puncture needle having a second needle tip and configured to puncture the living body tissue, the second needle tip being oriented in a direction different from a direction in which the first needle tip is oriented, the second puncture needle being configured to be detachable in relation to the first puncture needle and movable relative to the first puncture needle in a proximal direction of the first puncture needle when the second needle tip punctures the living body tissue, and wherein the second puncture needle is inserted in the hollow portion so that the second puncture needle is movable relative to the first puncture needle along a longitudinal direction of the first puncture needle, and the first puncture needle having a region bent along the longitudinal direction of the first puncture needle and the second puncture needle having a region bent along a longitudinal direction of the second puncture needle; and
   a moving section configured to move the second puncture needle relative to the first puncture needle in the proximal direction of the first puncture needle.

10. The puncture apparatus according to claim 9, comprising:
    an opening communicating with the hollow portion of the first puncture needle on a proximal portion of the first puncture needle; and
    the second puncture needle being configured to protrude through the opening when the second puncture needle is moved relative to the first puncture needle in the proximal direction of the first puncture needle.

11. The puncture apparatus according to claim 9, wherein the moving section has a traction wire for pulling the second puncture needle toward the second needle tip.

12. The puncture apparatus according to claim 9, wherein the moving section has a pushing member, which has an elongated shape and is configured to push the second puncture needle toward the second needle tip.

13. A method of forming a path in a living body tissue, the method comprising:
    puncturing the living body tissue with a first puncture needle having a first needle tip, the first puncture needle having a distal end and a proximal end, the first needle tip being on the distal end of the first puncture needle and being detachable from the first puncture needle, the first puncture needle having a hollow portion;
    inserting a second puncture needle in the hollow portion so that the second puncture needle is movable relative to the first puncture needle along a longitudinal direction of the first puncture needle, and the first puncture needle having a region bent along the longitudinal direction of the first puncture needle and the second puncture needle having a region bent along a longitudinal direction of the second puncture needle; and
    puncturing the living body tissue with the second puncture needle having a second needle tip, the second needle tip being oriented in a direction different from a direction in which the first needle tip is oriented, the second puncture needle being configured to be detachable in relation to the first puncture needle and movable relative to the first puncture needle in a proximal direction of the first puncture needle when the second needle tip punctures the living body tissue.

14. The method according to claim 13, comprising:
    pulling on a traction wire, which moves the second puncture needle toward the second needle tip.

15. The method according to claim 13, comprising:
    pushing the second puncture needle toward the second needle tip using a pushing member.

* * * * *